US006723329B2

(12) United States Patent
Johnston et al.

(10) Patent No.: US 6,723,329 B2
(45) Date of Patent: Apr. 20, 2004

(54) USE OF PARAPOX B2L PROTEIN TO MODIFY IMMUNE RESPONSES TO ADMINISTERED ANTIGENS

(75) Inventors: Stephen A. Johnston, Dallas, TX (US); Michael J. McGuire, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 4 days.

(21) Appl. No.: 10/414,759

(22) Filed: Apr. 15, 2003

(65) Prior Publication Data

US 2004/0054159 A1 Mar. 18, 2004

Related U.S. Application Data

(63) Continuation of application No. PCT/US02/38971, filed on Dec. 6, 2002.
(60) Provisional application No. 60/336,694, filed on Dec. 7, 2001.
(51) Int. Cl.[7] ........................ A61K 45/00; A61K 39/275
(52) U.S. Cl. ................................... 424/278.1; 424/232.1
(58) Field of Search ........................... 424/278.1, 232.1

(56) References Cited

U.S. PATENT DOCUMENTS

2003/0109483 A1 * 6/2003 Cassell et al. ................ 514/44

FOREIGN PATENT DOCUMENTS

| WO | 95/22978 | * | 9/1995 | .......... A61K/35/76 |
| WO | 97/37031 | * | 9/1997 | .......... C12N/15/86 |

OTHER PUBLICATIONS

Buttner (Develop. Biol. Standard. 65:221–226, 1986).*
Sullivan et al (Virology 202:968–973, 1994).*

* cited by examiner

*Primary Examiner*—Mary E. Mosher
(74) *Attorney, Agent, or Firm*—Richard Aron Osman

(57) ABSTRACT

The Parapox B2L virus envelope protein is used as an adjuvant to enhance a subject's response to an administered antigen. Both antibody and cellular immune responses can be modified. B2L protein is particularly useful as an adjuvant for poorly immunogenic tumor vaccines and subunit vaccines, such as those useful for preventing and/or treating flu, tuberculosis, respiratory syncytial virus, anthrax and HIV.

13 Claims, No Drawings

SEQUENCE LISTING

```
<160> NUMBER OF SEQ ID NOS: 4

<210> SEQ ID NO 1
<211> LENGTH: 1137
<212> TYPE: DNA
<213> ORGANISM: PARAPOX

<400> SEQUENCE: 1
atgtggccgt tctcctccat ccccctgggc gccgactgcc gcgtcgtgga gacgctgccc      60
gcagaggtgg cgtctttggc gcagggcaac atgagcaccc tcgactgctt caccgctatc     120
```

-continued

```
gccgagtccg cgaagaagtt cttgtacatc tgcagcttct gctgcaacct gagctccacc     180
aaggagggcg tcgacgtcaa ggacaagctc tgcacgctcg ccaaggaggg cgtagacgtc     240
acgctgctcg tggacgtgca gagcaaggac aaggacgcgg acgagctgcg cgaggcgggc     300
gtcaactact acaaggtcaa ggtgtccacc aaggagggcg tcggcaacct ctcggcagc      360 ttctggctct cggacgccgg gcactggtac gtgggaagcg cctcgctcac gggcgggtcc     420
gtgtccacca tcaagaacct cgggctctac tccaccaaca agcacctggc ctgggacctc     480
atgaaccgct acaacacctt ctactccatg atcgtggagc cgaaggtgcc gttcacgcgg     540
ctctgctgcg ccatcgtcac gcccacggcc acgaacttcc acctcgacca ctccggggc     600 ggcgtattct ctcggactc gccggagcgc ttcctaggct tctaccgcac gctcgacgag     660
gacctcgtgc tgcaccgcat cgagaacgcc aagaacagca tcgacctctc gctgctctcg     720
atggtgccgg tgatcaagca cgccagcgcc gtggagtact ggccgcagat cattgacgcg     780
ctgctgcgcg cggccatcaa ccgcggcgtg cgcgtgcgcg tgatcattac cgagtggaag     840
aacgcggacc cgctttcggt ctcggccgcg cgcagcctcg acgactttgg cgtcggcagc     900
gtggacatgt ccgtgcgcaa gttcgtggta cccggccggg acgacgccgc gaacaacact     960
aagctgctca tcgtggacga caccttcgcg cacctcacgg tcgccaacct cgacggcacg    1020
cactaccgct accacgcctt cgtgagcgtg aacgccgaga agggcgacat cgtcaaggac    1080
ctgtccgcgg tcttcgagcg ggactggcgc tcggagttct gcaagccaat aaattaa      1137
```

<210> SEQ ID NO 2
<211> LENGTH: 378
<212> TYPE: PRT
<213> ORGANISM: PARAPOX

<400> SEQUENCE: 2

```
Met Trp Pro Phe Ser Ser Ile Pro Leu Gly Ala Asp Cys Arg Val Val
 1               5                  10                  15

Glu Thr Leu Pro Ala Glu Val Ala Ser Leu Ala Gln Gly Asn Met Ser
            20                  25                  30

Thr Leu Asp Cys Phe Thr Ala Ile Ala Glu Ser Ala Lys Lys Phe Leu
        35                  40                  45

Tyr Ile Cys Ser Phe Cys Cys Asn Leu Ser Ser Thr Lys Glu Gly Val
    50                  55                  60

Asp Val Lys Asp Lys Leu Cys Thr Leu Ala Lys Glu Gly Val Asp Val
65                  70                  75                  80

Thr Leu Leu Val Asp Val Gln Ser Lys Asp Lys Asp Ala Asp Glu Leu
                85                  90                  95

Arg Glu Ala Gly Val Asn Tyr Tyr Lys Val Lys Val Ser Thr Lys Glu
            100                 105                 110

Gly Val Gly Asn Leu Leu Gly Ser Phe Trp Leu Ser Asp Ala Gly His
        115                 120                 125

Trp Tyr Val Gly Ser Ala Ser Leu Thr Gly Gly Ser Val Ser Thr Ile
    130                 135                 140

Lys Asn Leu Gly Leu Tyr Ser Thr Asn Lys His Leu Ala Trp Asp Leu
145                 150                 155                 160

Met Asn Arg Tyr Asn Thr Phe Tyr Ser Met Ile Val Glu Pro Lys Val
                165                 170                 175

Pro Phe Thr Arg Leu Cys Cys Ala Ile Val Thr Pro Thr Ala Thr Asn
            180                 185                 190
```

```
Phe His Leu Asp His Ser Gly Gly Val Phe Phe Ser Asp Ser Pro
        195                 200                 205

Glu Arg Phe Leu Gly Phe Tyr Arg Thr Leu Asp Glu Asp Leu Val Leu
        210                 215                 220

His Arg Ile Glu Asn Ala Lys Asn Ser Ile Asp Leu Ser Leu Leu Ser
225                 230                 235                 240

Met Val Pro Val Ile Lys His Ala Ser Ala Val Glu Tyr Trp Pro Gln
                245                 250                 255

Ile Ile Asp Ala Leu Leu Arg Ala Ala Ile Asn Arg Gly Val Arg Val
                260                 265                 270

Arg Val Ile Ile Thr Glu Trp Lys Asn Ala Asp Pro Leu Ser Val Ser
        275                 280                 285

Ala Ala Arg Ser Leu Asp Asp Phe Gly Val Gly Ser Val Asp Met Ser
        290                 295                 300

Val Arg Lys Phe Val Val Pro Gly Arg Asp Asp Ala Ala Asn Asn Thr
305                 310                 315                 320

Lys Leu Leu Ile Val Asp Asp Thr Phe Ala His Leu Thr Val Ala Asn
                325                 330                 335

Leu Asp Gly Thr His Tyr Arg Tyr His Ala Phe Val Ser Val Asn Ala
                340                 345                 350

Glu Lys Gly Asp Ile Val Lys Asp Leu Ser Ala Val Phe Glu Arg Asp
        355                 360                 365

Trp Arg Ser Glu Phe Cys Lys Pro Ile Asn
        370                 375

<210> SEQ ID NO 3
<211> LENGTH: 1137
<212> TYPE: DNA
<213> ORGANISM: PARAPOX

<400> SEQUENCE: 3
atgtggccgt tctcctccat ccccgtgggc gcccaatgcc gcgtcttgga aacgctgccc     60
gcagaggtgg cgtccctggc gcagggcaac atgagcaccc tcgactgctt caccgccatc    120
gccgagtccg cgaagaaatt tttgtacatc tgcagcttct gctgcaacct gagctccacc    180
aaggagggcg tcgacgtcaa agacaagctc tgcacgctcg ccaaggaagg cgttgacgtc    240
acgctgctcg tggacgtgca gagcaaggac aaggacgcgg acgaactgcg cgcggcgggc    300
gtcaactact acaaggtcaa agtgtccacg cgggaaggcg tcggcaacct ctcggcagc    360 ttctggctct cggacgccgg gcactggtac gtgggcagcg cctcgctcac gggcgggtcc    420
gtgtccacca tcaagaacct cgggctctac tccaccaaca agcacctggc ctgggacctc    480
atgaaccgct acaacacctt ctactccatg atcgtggagc gaaggtgcc gttcacgcgg    540 ctctgctgcg ccgtcgtcac gcccacggcc acgaacttcc acctcaacca ctccgggggc    600
ggcgtattct tctcggactc gccggagcgc ttcctaggct tctaccgcac gctcgacgag    660
gacctcgtgc tgcaccgcat cgagaacgcc aagaacagca tcgacctctc gctgctctcg    720
atggtgccgg tgatcaagca cgccggcgcc gtggagtact ggccgcggat catagacgcg    780
ctgctgcgcg cggccatcaa ccgcggcgtg cgcgtgcgcg tgatcatcac cgagtggaag    840
aacgcggacc cgctgtcggt ctcggccgcg cgcagcctcg acgactttgg cgtcggtagc    900
gtggacatgt ccgtgcgcaa gttcgtggta cccggccggg acgacgctgc gaacaacacc    960
aagctgctta cgtggacga caccttcgcg cacctcacgg tcgccaacct cgacggcacg   1020
```

```
cactaccgct accacgcctt cgtgagcgtg aacgccgaga agggcgacat cgtcaaggac    1080
ctgtccgcgg tcttcgagcg ggactggcgc tcggagtttt gcaagccaat aaattaa      1137
```

<210> SEQ ID NO 4
<211> LENGTH: 378
<212> TYPE: PRT
<213> ORGANISM: PARAPOX

<400> SEQUENCE: 4

```
Met Trp Pro Phe Ser Ser Ile Pro Leu Gly Ala Gln Cys Arg Val Leu
 1               5                  10                  15

Glu Thr Leu Pro Ala Glu Val Ala Ser Leu Ala Gln Gly Asn Met Ser
            20                  25                  30

Thr Leu Asp Cys Phe Thr Ala Ile Ala Glu Ser Ala Lys Lys Phe Leu
        35                  40                  45

Tyr Ile Cys Ser Phe Cys Cys Asn Leu Ser Ser Thr Lys Glu Gly Val
    50                  55                  60

Asp Val Lys Asp Lys Leu Cys Thr Leu Ala Lys Glu Gly Val Asp Val
65                  70                  75                  80

Thr Leu Leu Val Asp Val Gln Ser Lys Asp Lys Asp Ala Asp Glu Leu
                85                  90                  95

Arg Ala Ala Gly Val Asn Tyr Tyr Lys Val Lys Val Ser Thr Arg Glu
            100                 105                 110

Gly Val Gly Asn Leu Leu Gly Ser Phe Trp Leu Ser Asp Ala Gly His
        115                 120                 125

Trp Tyr Val Gly Ser Ala Ser Leu Thr Gly Gly Ser Val Ser Thr Ile
    130                 135                 140

Lys Asn Leu Gly Leu Tyr Ser Thr Asn Lys His Leu Ala Trp Asp Leu
145                 150                 155                 160

Met Asn Arg Tyr Asn Thr Phe Tyr Ser Met Ile Val Glu Pro Lys Val
                165                 170                 175

Pro Phe Thr Arg Leu Cys Cys Ala Val Val Thr Pro Thr Ala Thr Asn
            180                 185                 190

Phe His Leu Asn His Ser Gly Gly Val Phe Ser Asp Ser Pro
        195                 200                 205

Glu Arg Phe Leu Gly Phe Tyr Arg Thr Leu Asp Glu Asp Leu Val Leu
    210                 215                 220

His Arg Ile Glu Asn Ala Lys Asn Ser Ile Asp Leu Ser Leu Leu Ser
225                 230                 235                 240

Met Val Pro Val Ile Lys His Ala Gly Ala Val Glu Tyr Trp Pro Arg
                245                 250                 255

Ile Ile Asp Ala Leu Leu Arg Ala Ala Ile Asn Arg Gly Val Arg Val
            260                 265                 270

Arg Val Ile Ile Thr Glu Trp Lys Asn Ala Asp Pro Leu Ser Val Ser
        275                 280                 285

Ala Ala Arg Ser Leu Asp Asp Phe Gly Val Gly Ser Val Asp Met Ser
    290                 295                 300

Val Arg Lys Phe Val Val Pro Gly Arg Asp Asp Ala Ala Asn Asn Thr
305                 310                 315                 320

Lys Leu Leu Ile Val Asp Asp Thr Phe Ala His Leu Thr Val Ala Asn
                325                 330                 335

Leu Asp Gly Thr His Tyr Arg Tyr His Ala Phe Val Ser Val Asn Ala
            340                 345                 350
```

-continued

```
Glu Lys Gly Asp Ile Val Lys Asp Leu Ser Ala Val Phe Glu Arg Asp
        355                 360                 365

Trp Arg Ser Glu Phe Cys Lys Pro Ile Asn
370                 375
```

USE OF PARAPOX B2L PROTEIN TO MODIFY IMMUNE RESPONSES TO ADMINISTERED ANTIGENS

This application is a continuation under 35USC120 of PCT application No. PCT/US02/38971, filed Dec. 6, 2002, published as WO 03050135 on Jun. 19, 2003, which claims the benefit of provisional application Serial No. 60/336,694 filed Dec. 7, 2001.

This invention was funded in part by DARPA Grant No N652369915426, Account number 36001, by which the US Government may have certain rights in this invention.

FIELD OF THE INVENTION

The invention relates to the use of a B2L viral envelope protein of a Parapox virus as a vaccine adjuvant.

BACKGROUND OF THE INVENTION

Cutaneous Parapox virus ovis causes recruitment of epidermal dendritic cells to the infection site in sheep and subsequent cell-mediated immunity (Lear et al., Eur. J. Dermatol. 6, 135–40, 1996; Haig et al., Comp Immun. Microbiol. Infect. Dis. 20 197–204, 1997). Attenuated Parapox viruses can be used to induce Paradox-specific immunity. U.S. Pat. No. 6,162,600. In addition, the highly attenuated strain D1701 (Baypamun HK®) is used as a non-specific immunomodulator (Buttner et al., Immunol. Microbiol. Infect. Dis. 16, 1–10, 1993) to promote immunity to heterologous pathogens.

Attenuation of Parapox virus, however, is time-consuming, taking from 100 to 200 culture passages; according to WO 95/22978, it takes from three to five years to perform each 100 passages, depending on the species of virus used. Attenuation can, therefore, "encompass a period lasting from ten to twenty years." See WO 95/22978, page 9.

WO 95/22978 discloses the use of combinations of two or more individual Parapox virus components as "multipotent paramunity inducers" for use as adjuvant therapy for tumors and the prevention of metastases. The components can be individual polypeptides or detached envelopes of poxviruses. WO 95/22978, however, does not disclose any particular viral polypeptides other than the viral fusion protein and adsorption protein. Moreover, WO 95/22978 teaches that the disclosed paramunity inducers have virtually no immunogenic properties.

There is a need in the art for simple, effective vaccine adjuvants that can be used to enhance immune responses against tumors and dysplastic lesions and against exogenous pathogens.

SUMMARY OF THE INVENTION

It is an object of the invention to provide reagents and methods for modifying immune responses to administered antigens. This and other objects of the invention are provided by one or more of the embodiments described below.

One embodiment of the invention provides a method of enhancing an immune response to a vaccine composition. The method involves administering to a subject in need thereof (a) an effective amount of a B2L viral envelope protein of a Parapox virus and (b) a vaccine composition comprising an active component. The adjuvant B2L viral envelope protein thereby enhances the immune response to the vaccine composition.

Another embodiment of the invention provides a pharmaceutical composition comprising a B2L viral envelope protein of a Parapox virus and a vaccine composition comprising an active component.

Yet another embodiment of the invention provides a pharmaceutical composition comprising a nucleic acid molecule encoding a B2L viral envelope protein of a Parapox virus and a vaccine composition comprising an active component.

Thus, the invention provides pharmaceutical compositions and methods using B2L protein to modify immune responses to administered antigens.

DETAILED DESCRIPTION OF THE INVENTION

The invention is based on the ability of a Parapox viral envelope protein termed "B2L" to act as an adjuvant, i.e., to augment or otherwise modify a subject's immune response to an administered antigen and/or an active component of a vaccine. Administered antigens include, but are not limited to, cells expressing tumor antigens, attenuated or killed pathogens and antigenic components thereof or nucleic acids encoding the antigenic components.

Both antibody and cellular immune responses can be modified. B2L protein is particularly useful as an adjuvant for poorly immunogenic tumor antigens and subunit vaccines, such as those useful for preventing and/or treating flu, tuberculosis, respiratory syncytial virus, anthrax and HIV.

B2L is the second open reading frame in the BamH1 B fragment of the Orf virus genome (Sullivan et al., Virology 202, 968–73, 1994). Prior work teaches that, as the activity of epitopes responsible for antigen-specific immunization decrease, adjuvant activity of the preparations increases. See WO 95/22978, page 4. B2L is an immunogenic protein; in fact, B2L protein is one of a few Orf virus proteins to which a strong antibody response can be mounted in sheep. Sullivan et al., 1994. Thus, it is surprising that purified B2L protein itself has adjuvant activity.

B2L proteins for use in the compositions and methods described herein are those of the Parapoxvirus genus, such as Orf virus (OV), particularly the Parapox ovis strains NZ2, NZ7, NZ10, and D1701. Orf viruses are reviewed in Robinson & Balassu, Vet. Bull 51, 771, 1981; Robinson & Lyttle, in Binns & Smith, eds., recombinant poxviruses, Chapter 9, pp. 306–17, CRC Press, Boca Raton, 1992. An amino acid sequence for the B2L protein of OV NZ2 is disclosed in Sullivan et al., Identification and characterization of an orf virus homologue of the vaccinia virus gene encoding the major envelope antigen p37K, Virology 202 (2), 968–73, 1994, and is shown in SEQ ID NO:2. A coding sequence for SEQ ID NO:2 is shown in SEQ ID NO:1. The amino acid sequences of the B2L proteins obtained from D1701 and NZ2 are highly conserved. The amino acid sequence of the D1701 protein is shown in SEQ ID NO:4. A coding sequence for SEQ ID NO:4 is shown in SEQ ID NO:3.

Purified B2L protein is separated from other compounds that normally associate with the B2L protein in the virus, such as other envelope components. A preparation of purified B2L protein is at least 80% pure; preferably, the preparations are 90%, 95%, or 99% pure. Purity of the preparations can be assessed by any means known in the art, such as SDS-polyacrylamide gel electrophoresis.

Purified B2L protein for use in compositions and methods of the invention can be purified from Parapox viruses or from cells infected by the viruses, by recombinant DNA methods, and by chemical synthesis. Purification methods include, but are not limited to, size exclusion chromatography, ammonium sulfate fractionation, ion exchange chromatography, affinity chromatography, and preparative gel electrophoresis.

B2L protein can be expressed recombinantly, after insertion of B2L coding sequences into an expression vector that contains the necessary elements for the transcription and translation of the inserted coding sequence. Maintenance of orf viruses in culture is disclosed in WO 97/37031. A preferred system for maintaining and expressing B2L protein is HKB11 cells transfected with B2L in a vector such as a p2ToP, pCEP4, or pcDNA3.1 vector (Invitrogen). Recombinantly produced B2L protein can be secreted into the culture medium and purified. Methods for producing proteins recombinantly are well known to those skilled in the art.

A B2L protein also can be produced using chemical methods to synthesize its amino acid sequence, such as by direct peptide synthesis using solid-phase techniques (Merrifield, J. Am. Chem. Soc. 85, 2149–2154, 1963; Roberge et al., Science 269, 202–204, 1995). Protein synthesis can be performed using manual techniques or by automation. Optionally, fragments of a B2L protein can be separately synthesized and combined using chemical methods to produce a full-length molecule.

"B2L protein" as used herein includes both functional portions of B2L and full-length or partial biologically active B2L variants. Biologically active variants (i.e., variants that possess adjuvant activity) comprise amino acid substitutions, insertions, and/or deletions with respect to the amino acid sequences shown in SEQ ID NOS:2 or 4. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine. Biologically active variants can comprise 1, 2, 3, 4, 5, 6, 7, 8, 9, 10, 12, 15, 18, 20, 25, or 30 or more conservative amino acid substitutions as long as adjuvant activity of the B2L variant is maintained.

Amino acid insertions or deletions are changes to or within an amino acid sequence. They typically fall in the range of about 1 to 5 amino acids (i.e., 1, 2, 3, 4, or 5). Guidance in determining which amino acid residues can be substituted, inserted, or deleted without abolishing biological or immunological activity of a B2L protein can be found using computer programs well known in the art, such as DNASTAR software. Biological activity of a B2L protein having an amino acid substitution, insertion, and/or deletion can be tested, for example, as described in Example 1.

Functional portions of B2L comprising, for example, 25, 50, 75, 100, 125, 150, 175, 200, 225, 250, 275, 300, 325, 350, 360, 370, 375, or 377 amino acids, also can be used in the compositions and methods of the invention, provided that the portions of B2L retain biological activity, e.g., the ability to enhance an immune response and/or exert a chemotactic effect on enriched dendritic cell populations.

Purified B2L protein can be used in pharmaceutical compositions. Pharmaceutical compositions of the invention can be used to boost immune responses in mammals, including laboratory animals (e.g., mice, rats, hamsters, guinea pigs), companion animals (e.g., dogs, cats), farm animals (e.g., horses, cows, sheep, pigs, goats), and humans.

Pharmaceutical compositions of the invention include a pharmaceutically acceptable carrier. Typically these will be sterile formulations in a diluent or vehicle that is free of pyrogenic components. Buffers, stabilizers, and the like can be included, as is known in the art. Optionally, pharmaceutical compositions include conventional adjuvants, such as aluminum hydroxide and aluminum phosphate (collectively commonly referred to as alum), saponins complexed to membrane protein antigens (immune stimulating complexes), pluronic polymers with mineral oil, killed mycobacteria in mineral oil, Freund's complete adjuvant, bacterial products, such as muramyl dipeptide, and lipopolysaccharides.

If desired, B2L protein can be coupled to an antigen. Means of making such molecules are well known in the art. For example, coupled molecules can be synthesized chemically or produced by covalently linking two polypeptide segments or by standard procedures in the art of molecular biology. Recombinant DNA methods can be used to prepare fusion proteins, for example, by making a DNA construct which comprises B2L coding sequences in proper reading frame with nucleotides encoding a polypeptide to be coupled with B2L and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

B2L-containing compositions are co-administered with a particular antigen or vaccine composition. "Co-administration" includes administration of B2L and the antigen or vaccine composition separately or in the same composition.

Vaccine compositions comprise one or more active components, e.g., a tumor antigen or an attenuated or killed pathogen or an antigenic component thereof. Antigenic components include any component that is recognized by cells of the immune system. Suitable tumor antigens include, but are not limited to, α-fetoprotein, BAGE, β-HCG, CEA, ESO, GAGE, gangliosides, Her-2/neu, HPV E6/E7, immunoglobulins, MAGE-1, MAGE-2, MAGE-3, MAGE-4, MAGE-12, MART-1, Melan-A, melanoma antigen gp75, gp100, MN/G250, MUC1, MUC2, MUC3, MUC4, MUC18, PSA, PSM, RAGE, ras, SART-1, telomerase, thyroperoxidases, tyrosinases, and p53.

Vaccine compositions also can include a pathogen. The pathogen can be, e.g., an attenuated or killed virus, bacterium, mycoplasm, parasite, yeast, fungus, prion, or a protozoan. Suitable pathogens include human immunodeficiency viruses, Herpes viruses, hepatitis viruses, pox viruses, flu viruses, measles, mumps, rubella, rabies, respiratory syncytial viruses, *Bacillus anthracis, Bordetella pertussis, Borrelia burgdorferi, Clostridium tetani, Corynebacterium diphtheriae, Haemophilus influenza B, Neisseria meningitidis, Salmonella typhi, Streptococcus pneumoniae,* and *Vibrio cholerae.* The active component also can be, for example, an immunogenic fragment, extract, subunit, metabolite, or recombinant construct of such a pathogen. Optionally, the active component can be mixed with a pharmaceutically acceptable carrier and/or a conventional adjuvant, as described above.

Adjuvant compositions comprising B2L protein can be administered sequentially or simultaneously with a vaccine composition, including a poorly immunogenic subunit vaccine. If desired, the B2L protein can be present in the vaccine composition. Suitable routes of administration include, without limitation, subcutaneous, intravenous, nasal, ophthalmic, transdermal, intramuscular, intradermal, intragastric, perlingual, alveolar, gingival, intraperitoneal, intravaginal, pulmonary, rectal, and oral administration. Administration can be by any suitable means, including injection, topical administration, ingestion, or inhalation. Single and/or multiple administrations are contemplated.

Optionally, B2L protein can be administered using a nucleic acid molecule encoding the protein. The nucleic acid molecule can be either DNA, RNA, or a DNA/RNA chimera. Use of DNA-encoded elicitors of immune responses is discussed, for example, in McDonnel & Askari, New Engl J. Med. 334, 42–45, 1996; Robinson, Can. Med. Assoc. J. 152, 1629–32, 1995; Fynan et al., Int. J. Immunopharmacol. 17, 79–83, 1995; Pardoll & Beckerleg, Immunity 3, 165–69, 1995, and Spooner et al., Gene Therapy 2, 173–80, 1995. Chimeric RNA/DNA oligonucleotide based gene therapy is discussed in Lai & Lien, Expert Opin Biol Ther 2001 January; 1(1):41–7.

A variety of delivery systems, both viral and non-viral, can be used to administer the B2L-encoding nucleic acid molecule. Such delivery systems include, but are not limited to, naked plasmid DNA, viral expression vectors, and nucleic acid molecules in conjunction with a liposome or a condensing agent. See U.S. Pat. No. 6,303,372.

The determination of a therapeutically effective dose of B2L is well within the capability of those skilled in the art. A therapeutically effective dose refers to that amount of active ingredient (i.e., B2L protein or nucleic acid encoding B2L) that results in an augmentation of the immune response to a co-administered antigen, compared to that which occurs in the absence of the therapeutically effective dose.

The therapeutically effective dose can be estimated initially either in cell culture assays or in animal models, usually mice, rats, rabbits, dogs, or pigs. The animal model also can be used to determine the appropriate concentration range and route of administration. Such information can then be used to determine useful doses and routes for administration in humans.

Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

Pharmaceutical compositions that exhibit large therapeutic indices are preferred. The data obtained from cell culture assays and animal studies are used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

Suitable dosages and treatment regimens for administration of either B2L protein or nucleic acid molecules encoding B2L include, but are not limited to, daily, twice-or three-times weekly, weekly, bi-weekly, monthly, bimonthly, or yearly treatments of about 1,5,10,15, 20, 25, 50, 75,100, or 200 ug/$m^2$ (or approximately 0.05, 0.1, 0.2, 0.25, 0.3, 0.5, 0.75,1, 2, 5, or 10 mg/kg). Preferred routes of administration include subcutaneous, intradermal, intramuscular administration. The exact dosage, treatment regimen, and route of administration, however, will be determined by the practitioner, in light of factors related to the subject that requires treatment.

All patents, patent applications, and references cited in this disclosure are expressly incorporated herein by reference in their entireties. The above disclosure generally describes the present invention. A more complete understanding can be obtained by reference to the following specific example, which is provided for purposes of illustration only and is not intended to limit the scope of the invention.

EXAMPLES

B2L provides adjuvant activity when coadministered with a tumor antigen. Tumor peptides frequently are weak immunogens, and immune responses to them typically require that they be administered together with an adjuvant. A tumor vaccine consisting of an emulsion prepared with Montanide ISA51 containing 100 ug of a melanoma peptide (TRP-2) and 100 ug of either V5His6-tagged B2L or and irrelevant protein (hSLC; human secondary lymphoid chemokine) was administered subcutaneously at the base of the tail three days after implantation of a melanoma tumor known to express the antigen included in the vaccine. Tumor growth was monitored until the nodules reached the volume permitted by an approved animal care and use protocol. By comparison with animals given the tumor antigen together with an irrelevant protein, there was a trend toward reduced tumor growth in mice treated with tumor antigen together with tagged B2L. The results are consistent with B2L's augmentation of an immune response to the TRP-2 tumor antigen, which slowed the growth of the tumor expressing this antigen.

What is claimed is:

1. A method of enhancing an immune response to an antigen, comprising the steps of:

administering to a subject mammal in need thereof (a) an effective amount of a B2L viral envelope protein of a Parapox virus, wherein the B2L protein is unassociated with other envelope components naturally associated with the B2L protein in the virus, and (b) an antigen, whereby the B2L protein acts as an adjuvant to enhance the immune response to the antigen; and detecting a resultant enhanced, specific immune response to the antigen.

2. The method of claim 1 wherein the B2L protein and the antigen are administered sequentially.

3. The method of claim 1 wherein the B2L protein and the antigen are administered simultaneously.

4. The method of claim 1 wherein the B2L protein and the antigen are administered simultaneously as a fusion protein comprising the B2L protein and the antigen.

5. The method of claim 1 wherein the B2L protein is administered by means of a nucleic acid encoding the B2L protein.

6. The method of claim 1 wherein the antigen is administered by means of a nucleic acid encoding the antigen.

7. The method of claim 1 wherein the antigen is administered as an attenuated or killed pathogen comprising the antigen.

8. The method of claim 1 wherein the antigen is a tumor antigen.

9. The method of claim 1 wherein the B2L protein and the antigen are administered by injection.

10. The method of claim 1 wherein the B2L protein and the antigen are administered intradermally.

11. The method of claim 1 wherein the Parapox virus is a Parapox virus ovis strain selected from the group consisting of NZ2, NZ7, NZ10, and D1701.

12. The method of claim 1 wherein the mammal is a human.

13. A pharmaceutical composition for enhancing an immune response to an antigen, the composition comprising:

a B2L viral envelope protein of a Parapox virus, or a nucleic acid encoding said B2L protein, wherein the B2L protein is unassociated with other envelope components naturally associated with the B2L protein in the virus; and an antigen or a nucleic acid encoding said antigen, wherein administered to a subject mammal in need thereof, the B2L protein of the pharmaceutical composition acts as an adjuvant to enhance a specific immune response to the antigen.

* * * * *